United States Patent [19]

Hauer et al.

[11] 4,443,220

[45] Apr. 17, 1984

[54] BLOOD COLLECTION AND TRANSFER APPARATUS

[76] Inventors: Jerome M. Hauer, 307 Auburndale Ave., Auburndale, Mass. 02166; Robert L. Thurer, 129 Pinckney St., Boston, Mass. 02114

[21] Appl. No.: 358,622

[22] Filed: Mar. 16, 1982

[51] Int. Cl.³ .............................................. A61M 5/14
[52] U.S. Cl. ...................................... 604/408; 604/4; 604/319
[58] Field of Search ........................................ 604/4–6, 604/8–10, 262, 408, 319; 128/DIG. 24; 248/95

[56] References Cited

U.S. PATENT DOCUMENTS 2,953,145 9/1960 Moss et al. ........................... 135/105
3,965,896 6/1976 Swank ..................................... 604/4
4,014,329 3/1977 Welch et al. ............................ 604/4

Primary Examiner—C. Fred Rosenbaum
Assistant Examiner—Sherri E. Vinyard
Attorney, Agent, or Firm—Kenway & Jenney

[57] ABSTRACT

Blood collection and transfer apparatus is adapted for autotransfusion in preoperative, operative and postoperative procedures. A collapsible bag is provided with a stent adapted to hold it in distended form when desired, whereby a negative gage pressure may be applied for blood collection. Fittings for controlled addition of anticoagulants may be included. The apparatus is useful in diverse settings, for example, chest trauma, postsurgical collection and reinfusion of mediastinal blood, collection and reinfusion of shed blood during surgery, cell washing procedures and cardiopulmonary procedure wherein it functions as a cardiotomy reservoir.

14 Claims, 5 Drawing Figures

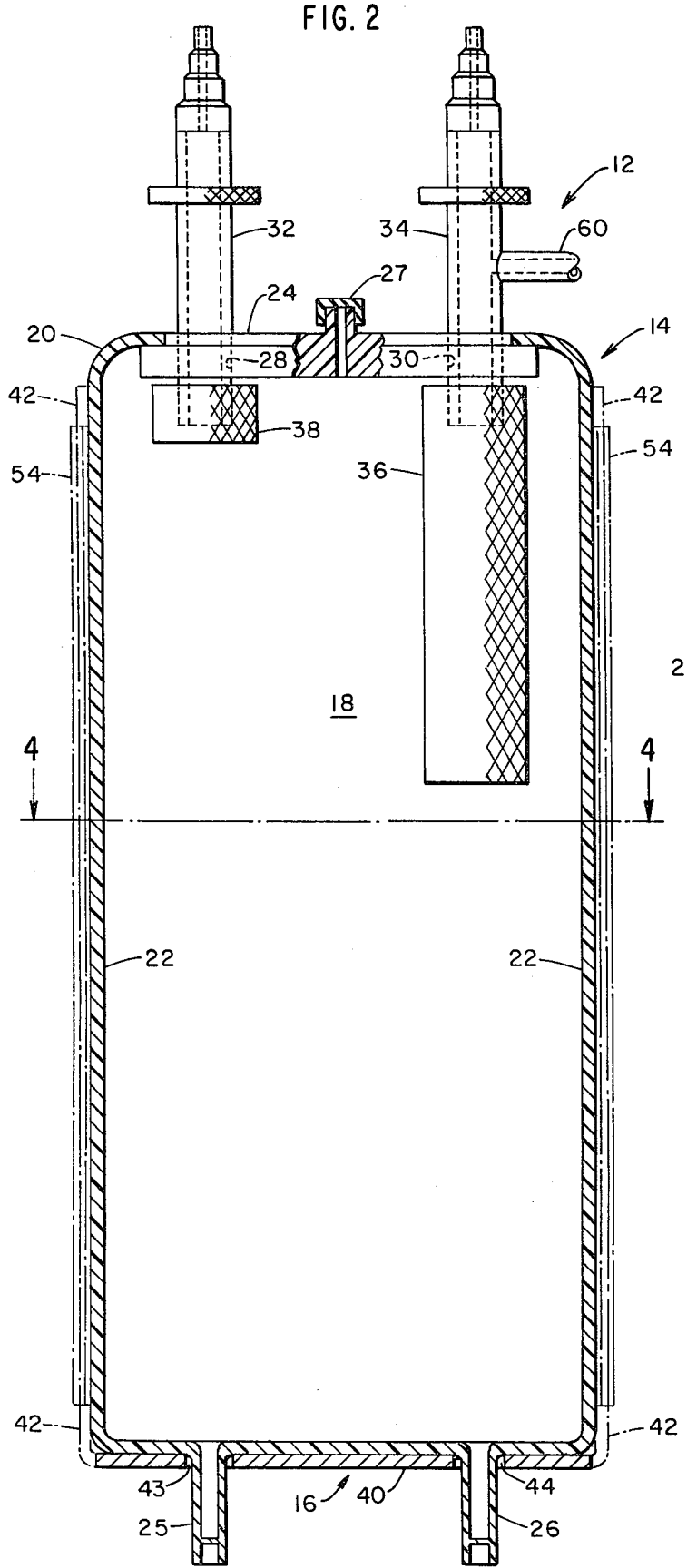

BLOOD COLLECTION AND TRANSFER APPARATUS

BRIEF SUMMARY OF THE INVENTION

This invention relates generally to apparatus for the collection, temporary storage and transfer of whole blood. More particularly, it relates to apparatus useful for autotransfusion, that is transfer by reinfusion to a patient of the patient's own blood, among other uses. This so-called autologous blood, to the extent that it may be in suitable condition for reinfusion, is superior to homologous blood, that is blood from other humans, for a number of medical reasons in addition to the obvious practical consideration that it reduces the use of bank blood available in the community. Well-known hazards in the use of homologous blood are (1) the transmission of infectious disease, notably hepatitis, (2) major histocompatibility reactions, (3) allergy and fever reactions, and (4) isoimmunization.

Circumstances in which autotransfusion may be used occur before, during and after surgery. In an emergency room setting it may be desired to collect and subsequently reinfuse blood lost through chest trauma. In an operating room setting, it may be desired to collect and reinfuse blood that is shed during surgery. This may apply to a large number of surgical procedures, but various forms of cardiotomy such as cardiopulmonary bypass are important examples. After cardiac surgery, occasions arise for the collection and reinfusion of shed mediastinal blood.

The concept of autotransfusion is old, but its implementation in practice has been incomplete and obstructed by certain difficulties that have not been completely overcome. In particular, the administration of collected blood may be complicated by air embolization, inadequate, excessive or improper administration of anticoagulating agents, and excessive trauma to the blood elements. An upsurge of autotransfusion techniques occurred in the 1960's with the introduction of a number of devices designed specifically for this procedure. (Dyer, 1966 and Klebanoff, 1968) The new devices have been able to reduce, but not to eliminate totally, the above-mentioned difficulties.

With a view to providing improved apparatus for autotransfusion, specifically addressed to the above-mentioned difficulties and for the further obvious purpose of achieving better sterile conditions, this invention features the use of a collapsible, sterilizable collection bag in combination with a special stent adapted to hold the bag in distended form as blood is collected in the presence of a vacuum in the bag. The means provided for holding the bag in distended form are readily releasable, allowing the bag to collapse during transfer of blood to the patient, to a cell washer, to an oxygenator or to some other receiver.

The improved apparatus can be adapted for the addition of anticoagulants to the collected blood in controlled quantities as a function of the quantity of blood collected. Filters can be located to exclude masses of a predetermined size or larger from the contents of the collection bag, during both the collection and blood transfer phases in use.

The stent structure provides a means for supporting the collection bag by allowing it to be either free-standing or attached as by clamping to a pole or the like.

Other features of the invention will be evident from the following description of the presently preferred embodiment, having reference to the appended drawings.

BRIEF DESCRIPTION OF THE DRAWINGS

FIG. 2 is an elevation in section of the apparatus of FIG. 1.

FIG. 3 is a partial view in perspective of the stent.

FIG. 4 is a view in section taken on line 4—4 of FIG. 2.

FIG. 5 is a view of the apparatus in configuration for the transfer of previously collected blood.

DETAILED DESCRIPTION

Figure 1:
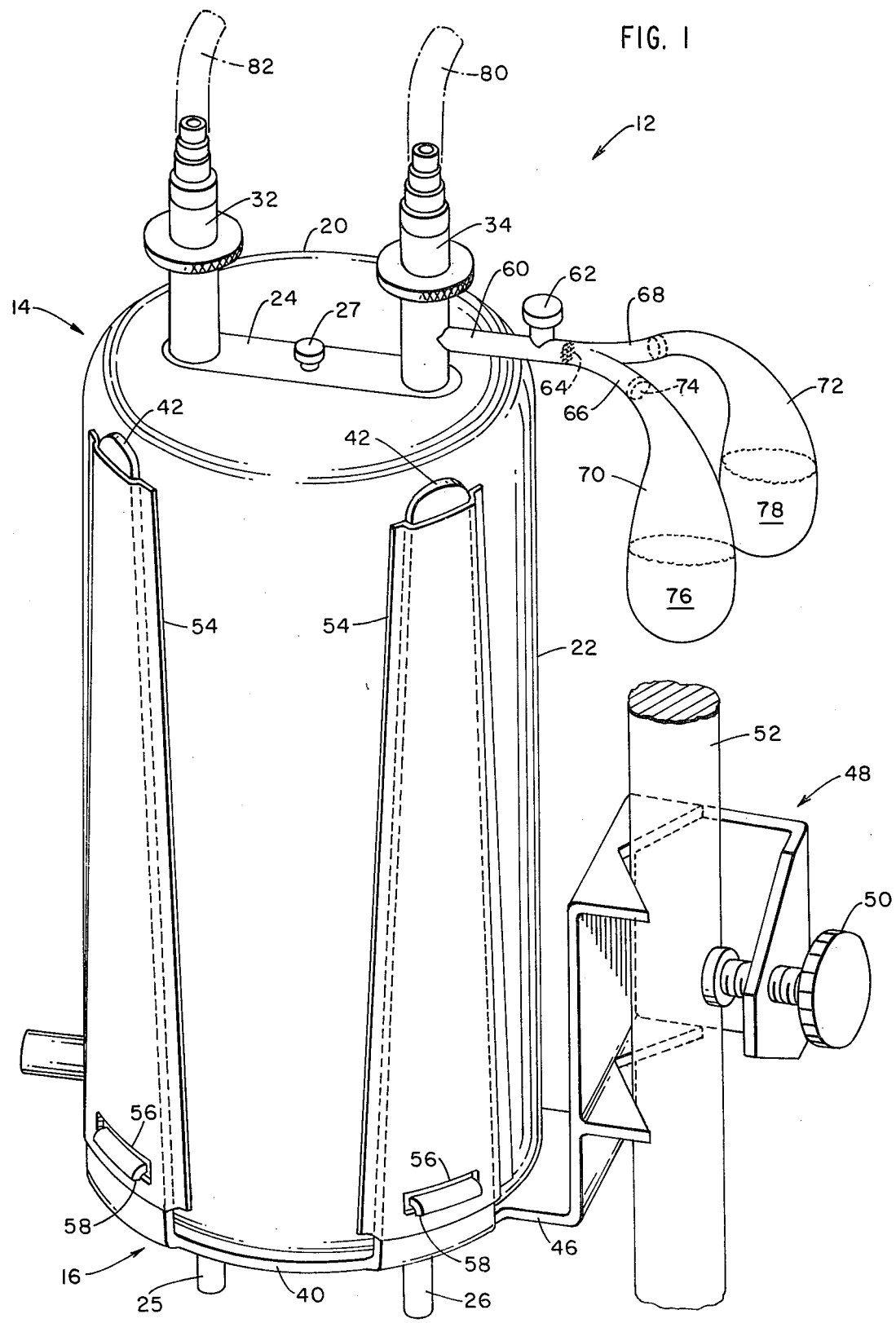
FIG. 1 is a view in perspective of the presently preferred embodiment of a blood collection and transfer apparatus according to this invention.

Referring to the drawings, the presently preferred form of the invention is designated as a whole at 12. The principal components comprise a collapsible collection bag 14 and a stent 16 that may be optionally assembled with the bag to hold it in distended form, or separated from the bag to allow it to collapse during the transfer of blood therefrom.

The bag is preferably a disposable subassembly forming a collapsible, sterilizable enclosure 18, and includes a foldable fabric body 20 formed of a suitable biocompatible material such as polyvinylchloride sheet material. The body is of generally cylindrical form with an annular side wall portion 22. The body 20 is attached to a plate 24, overlapping the plate on its top surface, the plate comprising another part of the bag 14. The means of attachment may consist of adhesive or fusion with heat. Alternatively, the body and plate may be formed integrally, as by molding. At the bottom of the bag, the body 20 has a pair of integrally molded tubes 25 and 26 each closed by an integrally molded diaphragm. These diaphragms are thin enough to be readily spiked with a standard filtered blood infusion set when the contents of the bag are to be transferred to the patient or to receiving apparatus.

The plate 24 is fitted with a rubber cap 27 closing a port into which a needle may be injected as described below to evacuate air from the bag. The plate 24 also has a pair of openings 28 and 30, each fitted with port means comprising tubes 32 and 34, respectively, each projecting into the enclosure 18 and extending externally of the enclosure. For adaptation to various sizes of fittings the end portion of each of the tubes 32 and 34 preferably has a stepped configuration.

The tube 34 comprises intake port means and is adapted for tubal connection with standard devices such as chest tubes, suction wands and the like. Within the enclosure, the tube 34 is fitted with a 170-micron screen filter 36 for collecting clots and particulate matter entering through the tube.

The tube 32 is also fitted with a 170-micron screen filter 38 of smaller size than the filter 36, for use during the blood transfer phase of operation as described below. The tube 32 may act as an air vent in certain procedures as described below, or alternatively it may be connected to a regulated vacuum pump or to the tube 34, the latter connection being illustrated in FIG. 5. Typically, the source of regulated vacuum applies a negative gage pressure to the enclosure 18. This may be of the order of minus 100 mm of mercury, which is a sufficient vacuum to collapse the bag in the absence of the restraint provided by the stent as hereinafter described.

The stent 16 is a rigid or semi-rigid member having a circular base 40 and a number of integral, parallel tines 42. Holes 43 and 44 are provided to accommodate the tubes 25 and 26. The tines 42 are tapered from the base toward their free ends. A lateral extension 46 from the base is formed into a clamp 48 receiving a clamp screw 50 for attachment to a pole 52. The stent may be fabricated of sheet metal as shown, or it may be formed of a suitable synthetic material. Preferably, it is constructed of durable material and is not required to be sterilized. Unlike the bag 14, the stent may be nondisposable.

For assembly with the stent, the bag 14 has a number of elongate sleeve-like fabric loops 54 attached to the outer surface of the body 20 in an annular arrangement. These loops may be formed of the same material as the body and may be secured thereto by adhesive or by fusion under heat. The loops are tapered to fit the tines 42, and near the wider ends the loops have apertures 56 to receive detents 58 formed integrally with and projecting outwardly from the tines 42.

For the frequent occasions when it is desired to add anticoagulants to the collected blood, the tube 34 is preferably provided with a branch 60 having a valve 62, an internal screen 64 and Y-branches 66 and 68. These branches are respectively fitted with side bags 70 and 72, each bag being provided with a rubber stopper 74. A pre-measured quantity 76 of anticoagulant such as citrate phosphate-dextrose solution or heparin solution is contained in the side bag 70, and a second premeasured quantity 78 of the same or any other desired solution is contained in the side bag 72. In a typical application the quantity of anticoagulant in each of the side bags is sufficient for about half of the full volume capacity of the bag, such capacity being typically 1200 ml. The stoppers are arranged so that upon manual squeezing of one of the side bags, its stopper is dislodged and trapped by the screen 64 in a manner which allows the contents to be expressed from the side bag into the branch tube 60 and through the tube 34 into the bag 14. Thus, if the bag 14 is only half-filled with blood the contents of only one of the side bags will be so added, whereas if the bag 14 is nearly full the contents of both of the side bags will be added.

The invention has many uses that demonstrate its advantages in dealing with the problems of air emboli, poorly controlled anticoagulation and the need for sterility maintenance throughout the collection and reinfusion or other transfer phases. The following describes typical procedures.

In an emergency room setting with chest trauma, the patient will have a standard chest tube in place and the chest tube will be connected by connecting tubing 80 to the intake port tube 34. The tube 32 will be connected by tubing 82 to a standard source of regulated suction (not shown). The bag 14 is held distended in place on the stent 16 as illustrated in FIGS. 1, 2 and 4. When blood is collected after chest trauma, anticoagulation may or may not be necessary. If it is not required the valve 62 is closed. If it is required, anticoagulant can be added by manually squeezing one or both of the side bags 70 and 72 at any time during the collection phase. During blood collection the bag 14 functions in a manner equivalent to that of a rigid collecting bottle, since it is held in distended form by the stent 16. For purposes of reinfusion of this collected blood, the bag 14 is first withdrawn from the stent 16 by slipping the tines 42 out of the loops 54, and the tubes 32 and 34 are interconnected either by turning and fitting them together or by the use of a tubal connector so as to form the configuration shown in FIG. 5. By means of the tubular loop so formed, or by other means suspending or attached to the bag 14, the bag is suspended on a projecting hook 84 attached to a standard pole 86. A hollow needle is next inserted in the cap 27 to create an opening and any air that may remain in the bag is evacuated through the needle by manually compressing the bag. The needle is then withdrawn and the bag is spiked through one of the tubes 25 or 26 with a standard filtered blood infusion set 88, and the blood is delivered to the patient by gravity or by pressure applied externally to the bag. In this phase the bag collapses as the blood is drawn from it.

Essentially the same procedure is followed in the use of the device following cardiac surgery for the collection and reinfusion of shed mediastinal blood. In this case the tubing 80 connects the intake port by way of a standard Y-connector to the chest tubes entering the mediastinum and/or the right and left thoracic cavities. Reinfusion of the blood takes place in the manner previously described.

The use of the device for the collection and reinfusion of shed blood during surgery is also basically similar to the above. In this case the connecting tubing 80 is attached to a standard suction wand placed in the surgical field. Regulated suction is applied through the tube 32 and citrate anticoagulant is added, both as described above. Reinfusion may be accomplished in the manner previously described and illustrated in FIG. 5; or alternatively, the infusion set 88 may be connected by its tubing 90 to a standard cell washing system (not shown).

In each of the above applications there is commonly a blood collecting phase during which the intake port tube 34 is connected to the patient and the bag is not yet spiked with the infusion set 88. This is followed by a transfer phase in which the tube 34 is interconnected with the tube 32 and the bag is spiked with the infusion set 88. During the latter phase, the filter 38 is in position to trap any clots or other particulate matter, previously trapped in the filter 36, that might otherwise be transferred from the filter 36 through the tube 34 to the tube 32 and the bag.

In certain procedures, the device may be connected in somewhat different configurations. One example occurs in the use of the device as an on-line reservoir for a cell washing system. In this case, the intake tube 34 may be connected to a field suction nozzle as in the operating procedure described above with the tube 32 connected to a source of vacuum. At the same time the bag is connected to the cell washer through one or two infusion sets spiked into one or both of the tubes 25 and 26. When the bag is being filled, the tube or tubes of each infusion set in use, such as the tube 90, is clamped by means of an external clamp. When it is desired to drain blood from the bag to the cell washer, the clamp is removed from the tube 90 and applied to the tube 82 to occlude the vacuum source. The blood then drains into the cell washer by gravity. Throughout this procedure, the bag 14 is assembled on the stent 16 as illustrated in FIGS. 1, 2 and 4.

A variation of the last-mentioned procedure occurs in the use of the device as a cardiotomy reservoir during cardiopulmonary bypass. In this case the bag 14, assembled on the stent 16 as shown in FIGS. 1, 2 and 4, is mounted by the clamp 48 to a pole mounted on a bypass machine. A disposable manifold of conventional form (not shown) is connected to the intake port tube 34, allowing the simultaneous connection of suction tubes to the intake port. In particular, cardiotomy suction and cardiac vent tubes are connected to this manifold. In addition, other fluids may be added through the intake port tube 34. In this case the tube 32 acts as an air vent. Two bottom spikes such as 88 are in place with their tubes such as 90 connected to a blood oxygenator. External tube clamps are employed as necessary during phases of collection and transfer of blood to and from the bag 14. After cardiopulmonary bypass, the bag may be thus filled with the residual pump contents of the bypass machine, and the bag 14 may be removed from the stent 16 to allow the collected material to be reinfused by gravity either directly to the patient or to a cell processing system.

The necessary functions of the stent 16 by which it holds the bag 14 in distended form, when desired, will be apparent from the foregoing examples. Therefore, it will also be apparent that the particular configurations of the stent engaging means on the bag and the bag engaging means on the stent may take various alternative forms. In general, such means preferably form an annular configuration about the bag so as to hold it appropriately distended. Also, the mode of engagement of the stent with the bag must have sufficient strength to hold the bag distended in the presence of negative gage pressures of the order of magnitude encountered in practice. If plural tines are employed, loops 54 of elongate, sleeve-like configuration may be used as shown, or the bag may have an annular array of shorter loops. Such loops may be located so that each tine passes through a plurality thereof.

Also, in place of tines that extend in a parallel manner longitudinally of the bag 14 as illustrated, a suitable stent may be formed of a member or members of noncollapsible construction performing the function of the tines but extending annularly about the bag. In this case the bag may have loops oriented in the manner of belt loops.

The stent may also be provided with means other than tines for the retention of the bag in distended form. For example, such means may employ the principles of the separable fastening device described in U.S. Pat. No. 3,009,235 issued Nov. 21, 1961 to De Mestral. This device employs two members each provided with a large number of closely spaced interengageable hooking elements, certain of the hooking elements comprising hooks and certain others of the hooking elements comprising loops. One of such members, such as loop material, may be fastened to the external surface of the bag 14 in any desired configuration. The member or members engageable therewith, such as hook material, may be permanently fastened to portions of the stent forming an annular configuration about the bag. In this manner the areas of the respective interengaging members may be selected to provide the necessary reaction force for resisting the tendency of the bag to collapse in the presence of a vacuum. The interengaging members may be quickly and easily manually disengaged whenever it is desired to remove the bag from the stent. Other alternative constructions of the stent and bag will also occur to one skilled in this art, subject to the requirement that the stent engaging means on the bag will permit it to collapse when it is removed from the stent.

What is claimed is:

1. Blood collection and transfer apparatus comprising, in combination,
    a collection bag comprising a foldable fabric forming a collapsible, sterilizable enclosure and having an annular side wall portion, said bag having a pair of openings each fitted with port means extending externally of the enclosure for a tubal connection, the side wall portion having collapsible stent engaging means forming an annular configuration thereabout and located externally of the enclosure, said bag being adapted for tubal connection separate from said pair of openings for transfer of blood therefrom, and
    a stent having noncollapsible bag engaging means formed in an annular configuration to surround the distended bag, said stent engaging means and bag engaging means being mutually engageable to hold the bag in distended form with a negative gage pressure on the enclosure, and mutually releaseable with the bag being in distended form to permit the bag to collapse upon the subsequent transfer of blood therefrom.

2. Apparatus according to claim 1, in which at least one of the port means includes a filter for blood entering the bag therethrough.

3. Apparatus according to claim 1, in which the port means are adapted for connection together or to separate tubing alternatively.

4. Apparatus according to claim 3, in which both of the port means include filters for blood entering the bag therethrough.

5. Apparatus according to claim 1, in which one of the port means has a portion external to the bag for plural tubal connections thereto.

6. Apparatus according to claim 5, in which at least one of the plural tubal connections is fitted with a collapsible, anticoagulant-filled side bag.

7. Apparatus according to claim 6, including plural tubal connections each fitted with a collapsible, anticoagulant-filled side bag.

8. Apparatus according to claim 1, in which the stent includes a bottom portion, the bag engaging means being elongate with an end thereof joined to the bottom portion.

9. Apparatus according to claim 8, in which the bottom portion includes a fitting for attachment to an external structure.

10. Apparatus according to claim 1, in which the bag has a noncollapsible top portion, said pair of openings passing through the top portion and said port means being fitted thereto.

11. Apparatus according to claim 1, in which the bag engaging means comprise a plurality of elongate tines.

12. Apparatus according to claim 11, in which the stent engaging means comprise a plurality of fabric loops each engageable with a tine by insertion of the tine therethrough.

13. Apparatus according to claim 12, in which the loops are elongate.

14. Apparatus according to claim 13, having at least one tine provided with a laterally extending detent and at least one loop provided with an aperture engageable with the detent for retaining the bag on the stent.

* * * * *